United States Patent [19]

Yamada et al.

[11] 3,983,176

[45] Sept. 28, 1976

[54] BENZOPHENONES AS PLANT GROWTH REGULANTS

[75] Inventors: Osamu Yamada; Akira Kurozumi; Shuichi Ishida; Fumio Futatsuya; Kensaku Ito; Hiroshi Yamamoto, all of Ageo, Japan

[73] Assignee: Nippon Kayaku Kabushiki Kaisha, Tokyo, Japan

[22] Filed: Nov. 14, 1974

[21] Appl. No.: 523,722

Related U.S. Application Data

[62] Division of Ser. No. 282,270, Aug. 21, 1972, Pat. No. 3,873,304.

[30] Foreign Application Priority Data

Aug. 24, 1971  Japan.............................. 46-64658

[52] U.S. Cl. ............................................... 260/591
[51] Int. Cl.[2]......................................... C07C 49/84
[58] Field of Search..................... 260/591; 424/331; 71/123

[56] References Cited

UNITED STATES PATENTS 2,671,016  3/1954  Erickson et al..................... 260/591
3,526,666  9/1976  Ponder................................ 260/591

OTHER PUBLICATIONS

Buu–Hoi et al., Bull. Soc. Chim France, 1955 pp. 1204–1207.
Eian et al., J. Org. Chem., vol. 32 (6), pp. 1864–1866 (1967).
Beelstein Handbook, 4th book, system 752, p. 1401.

Primary Examiner—James O. Thomas, Jr.
Assistant Examiner—James H. Reamer
Attorney, Agent, or Firm—Russell & Nields

[57] ABSTRACT

Novel plant growth regulants of the formula:

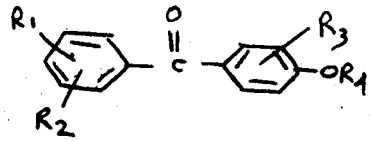

wherein $R_1$ and $R_2$, which may be the same or different, each represent hydrogen atoms or lower alkyl groups, $R_3$ is a lower alkyl group or a chlorine atom and $R_4$ is a lower alkyl group or an allyl group.

2 Claims, No Drawings

BENZOPHENONES AS PLANT GROWTH REGULANTS

This is a division of application Ser. No. 282,270 filed Aug. 21, 1972, now U.S. Pat. No. 3,873,304.

DETAILED DESCRIPTION OF THE INVENTION

Our extensive investigation on novel plant growth regulants have now led to the finding that compounds having the general formula (1);

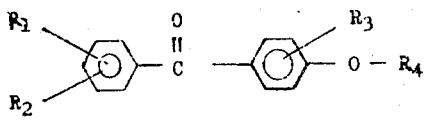

wherein $R_1$ and $R_2$, which may be the same or different, each represent hydrogen atoms or lower alkyl groups, $R_3$ is a lower alkyl group or a chlorine atom and $R_4$ is a lower alkyl group or an allyl group, have excellent plant growth regulatory properties, for example, effective for inhibiting seed germination, root elongation and plant (including algae) growth. This invention has been accomplished on the basis of the above finding.

Representative examples of compounds having the general formula (1) which are used as active ingredients in the plant growth regulants of this invention are as follows:

1. 2,2'-dimethyl-4-methoxybenzophenone, b.p. 140° – 142°C/2mmHg
2. 2,3'-dimethyl-4-methoxybenzophenone, b.p. 162.5° – 164.5°C/2.5mmHg
3. 2,4'-dimethyl-4-methoxybenzophenone, b.p. 160° – 161°C/15mmHg
4. 3-chloro-3'-methyl-4-methoxybenzophenone, m.p. 102° – 102.5°C
5. 3,3'-dimethyl-4-methoxybenzophenone, m.p. 62° – 65°C
6. 3,3'-dimethyl-4-ethoxybenzophenone, m.p. 51° – 53°C
7. 3-sec.-butyl-3'-methyl-4-methoxybenzophenone, b.p. 182° – 183°C/2mmHg
8. 3-isopropyl-3'-methyl-4-methoxybenzophenone, b.p. 175° – 176°C/2mmHg
9. 3,3'-dimethyl-4-n.-propoxybenzophenone, b.p. 171° – 172°C/2mmHg
10. 3,3'-dimethyl-4-allyloxybenzophenone, b.p. 177° – 178°C/2mmHg
11. 2,3',4'-trimethyl-4-methoxybenzophenone, b.p. 168° – 169°C/2.5mmHg
12. 3,3',5'-trimethyl-4-sec.-butoxybenzophenone, b.p. 170° – 175°C/1.5mmHg
13. 3-tert.-butyl-3'-methyl-4-methoxybenzophenone, m.p. 101.5° – 102.5°C
14. 2',3-dimethyl-4-methoxybenzophenone, m.p. 70° – 71.5°C
15. 3,4'-dimethyl-4-methoxybenzophenone, m.p. 75° – 76°C
16. 3,3',5'-trimethyl-4-methoxybenzophenone, m.p. 85° – 86°C
17. 2'-methyl-3-chloro-4-methoxybenzophenone, m.p. 105° – 106°C
18. 2,3'-dimethyl-4-ethoxybenzophenone, b.p. 180° – 181.5°C/3.5mmHg
19. 2,3'-dimethyl-4-sec.-butoxybenzophenone, b.p. 185° – 186°C/3mmHg
20. 3-methyl-4-methoxybenzophenone, m.p. 79.5° – 80.5°C
21. 2-methyl-4-methoxybenzophenone, m.p. 147° – 148°C/0.5mmHg
22. 3-chloro-4'-methyl-4-methoxybenzophenone, m.p. 107° – 108°C
23. 2,3',5'-trimethyl-4-methoxygenzophenone, b.p. 168° – 170°C/2mmHg
24. 3,3',4'-trimethyl-4-methoxybenzophenone, m.p. 98.5° – 99.5°C
25. 3-methyl-4-methoxy-4'-ethylbenzophenone b.p. 176° – 177°C/1mmHg
26. 3-methyl-4-methoxy-4'-n-butylbenzophenone b.p. 213° – 215°C/2mmHg
27. 3-methyl-4-methoxy-3'-n-propylbenzophenone b.p. 187.5° – 189.5°C/2mmHg Some of the compounds of this invention, for example, compound Nos. 4, 17, 20 and 21 are known compounds but have not yet been found to have any plant growth regulatory actions. These and other compounds of the invention may be prepared according to the so-called Friedel-Crafts reaction, usually in the presence of a solvent, as illustrated by the following reaction scheme:

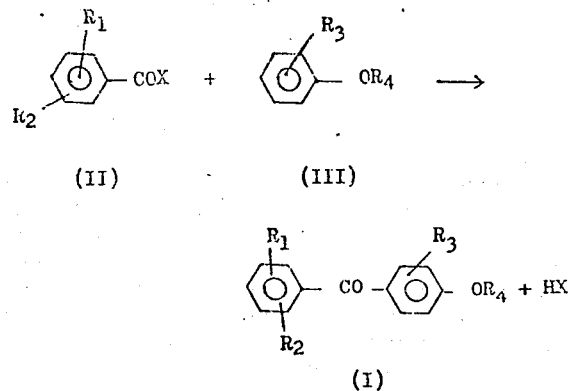

wherein X represents halogen atom, $R_1$ to $R_4$ have the same meanings as defined above, and $R_3$ is ortho or meta to the alkoxy group. Thus, for example, a Friedel-Crafts catalyst is first added to a compound of the general formula (III). Effective Friedel-Crafts catalysts include aluminum chloride, zinc chloride, ferric chloride, stannic chloride and titanium trichloride. The catalyst is used preferably in an equimolar to ca. 5% molar excess amount to the compound of the general formula (II) used. The use of a larger amount of the catalyst are not preferred since it may acceralate the cleavage of ether bonds present in compounds of the general formula (III) or (I). Subsequently, a compound of the general formula (II) is added dropwise. The compound of the general formula (II) is used preferably in an amount at most equimolar but in most cases ca. 5% lesser than equimolar. The reaction may be made to proceed more smoothly by using an inert solvent such as an aromatic or aliphatic hydrocarbon, carbon disulfide, nitroalkane or a chlorinated hydrocarbon solvent. When the compound of the general formula (II) is used in an amount approximately one half the amount of the compound of the general formula (III), the compound of the general formula (III) per se functions conveniently as a reaction medium. A temperature at which the compound of the general formula (II) is added dropwise is preferably within the range of from 0°C to 30°C. Simultaneously with the addition, the reaction takes place with hydrogen chloride being evolved. After the addition, the reaction temperature is raised and the reaction is continued until evolution of the hydrogen chloride is ceased. The reaction is completed usually in 2 to 5 hours. The reaction mixture is then cooled and poured into ice-water containing hydrochloric acid, and the separated product is isolated and purified in a conventional manner to obtain the desired product. In a somewhat modified manner, a compound of the general formula (II) is admixed with a compound of the general formula (III) and a catalyst is added to the resulting mixture. This process is particularly preferred when stannic chloride is used as the catalyst.

Below is an example of synthesis of the compounds of this invention.

Synthesis of 3,3'-dimethyl-4-methoxybenzophenone 13.3 Grams (0.1 mole) of aluminum chloride is added in small portions to a mixture of 18.3 g (0.15 mole) of o-methylanisole and 20 ml of benzene at a temperature not higher than 30°C. After the addition, 15.5 g (0.1 mole) of m-toluyl chloride is added dropwise to the mixture over 20 minutes while maintaining the temperature at or below 10°C. During this addition, a violent exothermic reaction takes place with hydrogen chloride being evolved. Thereafter, the reaction is continued at a temperature not higher than 20°C for 2 hours to give the reaction mixture which is a red viscous liquid. The reaction is further continued by keeping the mixture at 25° to 30°C for 1 hour. When the resulting reaction mixture is poured into a mixture of water (100 ml) and ice (100 g) containing a small amount of concentrated hydrochloric acid, the mixture is decomposed with evolution of heat whereby an organic substance is separated out. This organic substance is then extracted with 50 ml of benzene and the extract is washed twice with 5% sodium hydroxide and then with water, dried over anhydrous sodium sulfate and concentrated in vacuo to give 23.3 g (crude yield 97.1%) of a crude crystalline product. The crude product is then recrystallized from 30 ml of methanol to give 21.5 g (yield 89.5%) of a white crystalline product. M.P. 62° – 62.5°C.

Elemental analysis: Found : C 80.20%; H 6.70% Calculated: C 79.97%; H 6.71%

In the following Table 1 are shown several examples of synthesis of the same compound wherein the sorts of catalyst and solvent are changed.

Table 1

Examples of synthesis of 3,3'-dimethyl-4-methoxybenzophenone

| Amount of Compound (III) used (mol) 1) | Solvent | | Catalyst | | Temperatures (°C) at which Compound (II) is added dropwise | Reaction conditions | | Yield of Compound (I) (%) 2) |
|---|---|---|---|---|---|---|---|---|
| | Compound | Amount used (ml) | Compound | Amount used (mol) | | Temperature (°C) | Time (hrs) | |
| 2.0 | — | — | AlCl$_3$ | 1.0 | 5 – 10 | 25 | 3.5 | 75.7 |
| 1.1 | chlorobenzen | 50 | " | " | 10 or less | 25 – 30 | 3 | 85.4 |
| 1.3 | carbon disulfide | 400 | " | " | 5 | 25 | 2 | 78.7 |
| 1.1 | benzene | 50 | " | " | 10 | 25 – 30 | 2 | 70.0 |
| 1.5 | toluene | 30 | " | " | 5 – 7 | room temperature | 4.5 | 92.9 |
| " | nitrobenzene | 30 | " | " | 1 – 5 | " | 2.5 | 91.2 |
| " | ortho-dichlorobenzene | 30 | " | " | 5 | " | 5 | 89.3 |
| 2.0 | chlorobenzene | 30 | FeCl$_3$ | " | 2 – 3 | 20 – 25 / 25 – 27 / 25 | 2 / 2.5 / 1 | 84.1 |
| 1.1 | carbon disulfide | 450 | ZnCl$_2$ | " | 15 – 20 | 45 – 50 / 22 | 5 / 2.5 | 72.1 |
| 1.5 | 1,2-dichloroethane | 30 | SnCl$_3$ | " | 5 or less | 45 – 50 | 2 | 92.7 |
| " | — | — | TiCl$_3$ | " | 10 – 15 | room temperature | 2 | 95.7 |

1) Amount of compound (III) used is expressed in term of mole per mole of compound (II).
2) Yield of compound (I) is expressed in term of (crude yield) × (purity).

Other compounds of the invention can be synthesized in almost the same manner.

For actual use of the compounds of the invention as active ingredients in the plant growth regulant, they may be used as such or in admixture with a suitable carrier material to form emulsifiable concentrates, wettable powders, dusts, granules or tablets.

The application rate of the active ingredients of the invention may vary usually from 10 g to 100 g per are, preferably from 20 g to 80 g per are, although it depends, of course, upon the type of the area to be treated, the weed to be controlled, the particular active ingredient used and the like. The term "carrier material" is used herein to mean a vehicle or an extending agent with which the active ingredient is brought into contact with plants. Illustrative of solid carrier materials are clays, kaolin, talc, diatomaceous earth, silica and calcium carbonate. Illustrative of liquid carrier materials are benzene, alcohols, acetone, xylenes, methylnaphthalenes, cyclohexanone, dimethylformamide, dimethylsulfoxide, animal and vegetable oils, fatty acids and esters thereof and various surface active agents. The plant growth regulatory action may further be assured by jointly using a suitable conventional adjuvant such as a spreader, emulsifying agent, wetting agent and binding agent.

The active compounds of the invention may be used together with other herbicides such as 2-methylthio-4,6-bisisopropylamino-s-triazine (Prometryne), 2-methyl-thio-4,6-bisethylamino-s-triazine (Simetryne), S-(4-chlorobenzyl)-N, N-diethylthiolcarbamate (Saturn), isopropyl-N-(3-chlorophenyl)carbamate (Chloro-IPC), S-(β-benzene-sulfonylamidoethyl) O,O-diisopropyldithiophosphate and the like. In particular, satisfactory results are achieved when the compound of this invention is used in combination with the last mentioned S-(β-benzenesulfonylamidoethyl) O,O-diisopropyldithiophosphate.

The active ingredients of the invention may also be used in admixture with other agricultural bactricides, insecticides, nematocides, soil improvers, fertilizers and the like.

Excellent plant growth regulatory action of the active compounds of the invention will be demonstrated by the following examples.

EXAMPLE 1

1. Pre-emergence field test with the whole soil surface treated immediately after crop seeds sowing but before emergence of weeds Each of 1/5,000 are Wagner pots was charged with a given amount of a diluvian soil. A given number of seeds of crabgrass (Digitaria SPP.) and pigweed (Amaranthus SPP.) both predominant weeds found in usual dry field farming, were sown thereon and covered with the soil to a depth of about 0.5 cm. On these pots were separately sown 10 seeds per pot of each of soybean, cotton and sunflower and then covered with soil to a depth of 1.5 to 2 cm. Each liquid reagent diluted which with well water is scattered on the soil surface so that the active ingredient compound according to this invention may be 20, 40 and 80g per are respectively. Herbicidal activities and the growth conditions of crope are observed on the thirty days after the treatment. The results of observation are shown in the Table 2.

2. Paddy field: water application after the transplantation of paddy plant.

In each of 1/5,000 are Wagner pots was placed a given amount of alluvial paddy field soil and fertilizers were supplied in accordance with usual rice cultivation, to maintain the paddy field conditions similar to those usually found in cultivation in paddy fields. Thereafter, a given number of seeds of banyard grass (Echinochloa SPP.) was superficially incorporated into the top surface of the soil and two young rice seadling at three leave stage were transplanted. The irrigation water was kept at the level of about 0.5 cm until germination of banyard grass was observed. After the germination, the irrigation water level was raised to about 3 cm. When banyard grass reached 1.5 leave stage (usually 10 days after the transplantation), the liquid reagent diluted with water was applied to the individual pots so that the active ingredient compound according to this invention may be 20, 40 and 80 g per are respectively.

During the test, the irrigation water level was kept at 3 cm. After the treatment for 30 days, investigations were made for herbicidal action on barnyard glass and for presence or absence of influence on dry field crops and the aquatic rice plants as the degree of the influence, if any. The results are shown in Table 2.

Table 2

| Test compounds | Application rates (g/are) | Herbicidal effect[1] on | | | Influence on dry field crops[2] | | | Influence on paddy rice plants |
|---|---|---|---|---|---|---|---|---|
| | | crab grass | pigweed | barnyard grass | soybean | cotton | sunflower | |
| Compound of the invention 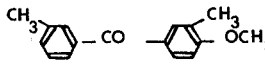 (compound No. 5) | 20 | 5 | 5 | 4.5 | — | — | — | — |
| | 40 | 5 | 5 | 5 | — | — | — | — |
| | 80 | 5 | 5 | 5 | — | — | — | — |
| Compound of the invention 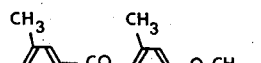 (compound No. 2) | 20 | 2 | 2 | 3 | — | — | — | — |
| | 40 | 4 | 4 | 4.5 | — | — | — | — |
| | 80 | 5 | 5 | 5 | — | — | — | — |
| Compound of the invention 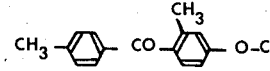 (compound No. 3) | 20 | 2 | 2 | 2 | — | — | — | — |
| | 40 | 3 | 3 | 3 | — | — | — | — |
| | 80 | 3.5 | 4 | 4 | — | — | — | — |
| Control 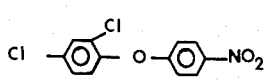 (Trade name NIP) | 20 | 3.5 | 5 | 5 | — | — | — | + |
| | 40 | 5 | 5 | 5 | ++ | +++ | +++ | ++ |
| | 80 | 5 | 5 | 5 | +++ | × | × | × |

Remarks:
[1] Ratings of herbicidal effect are defined in terms of the following numerals:
  5: Completely (100%) killed
  4: 80% killed
  3: 60% killed
  2: 40% killed
  1: 20% killed
  0: No herbicidal effect (The same number of weeds as in untreated Table 2-continued

| Test compounds | Application rates (g/are) | Herbicidal effect[1] on | | | Influence on dry field crops[2] | | | Influence on paddy rice plants |
|---|---|---|---|---|---|---|---|---|
| | | crab grass | pigweed | barnyard grass | soy-bean | cotton | sun-flower | | areas survived.)
2) Ratings of injuring effect on crops are defined in term of the following symbols:
    ×: Completely killed
++++: Severe injury
 +++: Medium injury
  ++: Slight injury
   +: Extremely slight injury
   −: No injury (Crops grew as in untreated areas.)

As is evident from Table 2, the active compounds of the invention have no influence upon the test crops, although the active compounds of the invention have extremely high safety in comparison with the control, they have approximately the same herbicidal effect as that of the control.

The following examples illustrate some influences of the active compounds of the invention on a variety of plants.

EXAMPLE 2

Influence on a variety of plants

In petri dishes of 9 cm diameter were placed sea sand to a depth of about 5 mm to provide seedling beds. Into these seedling beds were poured 10 ml per bed of each of the liquid compositions formulated in a manner such that the concentrations of the active compound of the invention might become, when applied, 500 and 100 ppm, respectively. Thereafter, 15 seeds of paddy plant, 15 seeds of barnyard grass, 50 seeds of manna-grass, 30 seeds of lucern, 20 seeds of tomato and 10 seeds of turnip were sown on individual petri dishes.

The assay was examined in an artificial climate chamber using light and darkness and temperature conditions alternating at 12 hour intervals; artificial illumination at 8000 luxes (at the point of the petri dishes) and temperature of 25°C for day time; no light (darkness) and temperature of 20°C for night time.

After the treatment for 14 days, investigations were made with the respective test plants for their growth condition. The results are shown in Table 3.

As are shown in Table 3, some of the active compounds of the invention have non-selective strong activity on all the tested plants, some of them have selective action on specific genera of plants and some show chlorosis action. Thus, the compounds of the invention have very interesting effects. Thus, the active compounds of this invention can be used as plant regulants or herbicides, taking advantage of such characteristics.

Table 3

| Test plant Application rates (ppm) Affected portions of plant* | rice plant | | | | barnyard grass | | | | crab-grass | | | | lucern | | | | turnip | | | | tomato | | | |
|---|---|---|---|---|---|---|---|---|---|---|---|---|---|---|---|---|---|---|---|---|---|---|---|---|
| | 500 | | 100 | | 500 | | 100 | | 500 | | 100 | | 500 | | 100 | | 500 | | 100 | | 500 | | 100 | |
| | T R | C | T R | C | T R | C | T R | C | T R | C | T R | C | T R | C | T R | C | T R | C | T R | C | T R | C | T R | C |
| Test compound No. 1 | 3 | | 0.5 | | 3 | | 2.5 | | 5 | | 5 | | 5 | | 3.5 | | 3 | | 2.5 | | 2 | | 1 | |
| | | 2.5 | | 1 | | 4.5 | | 4.5 | | 5 | | 5 | | 4 | | 3.5 | | 3.5 | | 3 | | 0 | | 0 |
| | 3.5 | | 1 | | 3.5 | | 2.5 | | 5 | | 5 | | 5 | | 4 | | 4.5 | | 3.5 | | 2 | | 2 | |
| 2 | 2 | | 1 | | 2 | | 2.5 | | 5 | | 5 | | 5 | | 5 | | 4 | | 3 | | 3 | | 1.5 | |
| | 2 | | 1 | | 5 | | 4 | | 5 | | 5 | | 5 | | 5 | | 4 | | 4 | | 0 | | 0 | |
| | 3 | | 1 | | 3 | | 3 | | 5 | | 5 | | 5 | | 5 | | 4.5 | | 4 | | 3 | | 1.5 | |
| 3 | 4 | | 1 | | 3 | | 2.5 | | 5 | | 5 | | 5 | | 5 | | 3 | | 2 | | 1.5 | | 1.5 | |
| | 1.5 | | 1 | | 4 | | 4 | | 5 | | 5 | | 0 | | 0 | | 4 | | 3.5 | | 0 | | 0 | |
| | 4 | | 1 | | 3 | | 3 | | 5 | | 5 | | 5 | | 5 | | 4 | | 2 | | 1.5 | | 1.5 | |
| 4 | 1 | | 0 | | 1 | | 0 | | 4 | | 4 | | 2 | | 0 | | 0 | | 0 | | 0 | | 0 | |
| | 0 | | 0 | | 1 | | 0.5 | | 1 | | 0 | | 0 | | 0 | | 0 | | 0 | | 0 | | 0 | |
| | 1 | | 0 | | 1 | | 0 | | 4.5 | | 4 | | 0 | | 0 | | 0 | | 0. | | 0 | | 0 | |
| | 2 | | 0 | | 3 | | 3 | | 5 | | 5 | | 5 | | 5 | | 4.5 | | 3.5 | | 5 | | 3.5 | |
| 5 | 4 | | 3 | | 5 | | 5 | | 5 | | 5 | | 5 | | 5 | | 5 | | 3 | | 5 | | 3 | |
| | 4 | | 1 | | 5 | | 4 | | 5 | | 5 | | 5 | | 5 | | 5 | | 3.5 | | 5 | | 3.5 | |
| | 0 | | 0 | | 4 | | 3 | | 5 | | 5 | | 1 | | 0 | | 0 | | 0 | | 0 | | 0 | |
| 6 | 0 | | 0 | | 5 | | 1 | | 5 | | 5 | | 0 | | 0 | | 0 | | 0 | | 0 | | 0 | |
| | 1 | | 0.5 | | 5 | | 4 | | 5 | | 5 | | 1 | | 0 | | 0 | | 0 | | 0 | | 0 | |
| 7 | 2 | | 1 | | 3 | | 0 | | 3 | | 2 | | 3.5 | | 0 | | 0 | | 0 | | 0 | | 0 | |
| | 0 | | 0 | | 0 | | 0 | | 0 | | 0 | | 0 | | 0 | | 0 | | 0 | | 0 | | 0 | |
| | 3 | | 1 | | 3 | | 0 | | 5 | | 1 | | 2.5 | | 0 | | 0 | | 0 | | 0 | | 0 | |
| | 3 | | 1 | | 2 | | 1 | | 5 | | 5 | | 3 | | 1 | | 3.5 | | 0 | | 1.5 | | 0 | |
| 1 | 0 | | 2 | | 2 | | 2 | | 5 | | 5 | | 0 | | 0 | | 0 | | 0 | | 0 | | 0 | |
| | 4 | | 1 | | 3 | | 1 | | 5 | | 5 | | 4.5 | | 1 | | 4.5 | | 0 | | 3 | | 0 | |
| | 2 | | 0 | | 1 | | 0 | | 4.5 | | 3.5 | | 1.5 | | 1 | | 1 | | 0 | | 1 | | 0 | |
| 9 | 1 | | 0 | | 2 | | 0 | | 5 | | 0 | | 0 | | 0 | | 0 | | 0 | | 0 | | 0 | |
| | 3 | | 0 | | 2.5 | | 0 | | 5 | | 2 | | 2.5 | | 0.5 | | 1.5 | | 1 | | 3 | | 1 | |
| | 0 | | 0 | | 0 | | 0 | | 5 | | 5 | | 1 | | 0.5 | | 0 | | 0 | | 0 | | 0 | |
| 10 | 0 | | 0 | | 1 | | 0 | | 5 | | 5 | | 1 | | 0.5 | | 0 | | 0 | | 0 | | 0 | |
| | 0 | | 0 | | 0 | | 0 | | 5 | | 5 | | 1.5 | | 0 | | 0 | | 0 | | 0 | | 0 | |
| | 2 | | 0 | | 2 | | 1 | | 4 | | 3.5 | | 2 | | 0.5 | | 2 | | 1 | | 1 | | 1 | |
| 11 | 1 | | 0 | | 1 | | 0 | | 5 | | 5 | | 1 | | 0 | | 0 | | 0 | | 0 | | 0 | |
| | 3 | | 1 | | 4 | | 3 | | 5 | | 4 | | 2 | | 0.5 | | 3 | | 2 | | 2 | | 1 | |
| | 2 | | 1 | | 1 | | 0 | | 4.5 | | 3 | | 1.5 | | 0.5 | | 0 | | 0 | | 1 | | 0 | |
| 12 | 1 | | 0 | | 2 | | 0 | | 5 | | 3 | | 0 | | 0 | | 0 | | 0 | | 0 | | 0 | |
| | 3 | | 0 | | 4 | | 1 | | 5 | | 2 | | 2.5 | | 0.5 | | 1.5 | | 1 | | 1 | | 0 | |

Table 3-continued

| Compound | Measure | rice 500 | rice 100 | barnyard 500 | barnyard 100 | crab-grass 500 | crab-grass 100 | lucern 500 | lucern 100 | turnip 500 | turnip 100 | tomato 500 | tomato 100 |
|---|---|---|---|---|---|---|---|---|---|---|---|---|---|
| 13 | T | 0 | 0 | 0 | 0 | 4.5 | 1.5 | 4.5 | 1 | 1 | 0.5 | 0 | 0 |
|  | R | 0 | 0 | 0 | 0 | 0 | 0 | 0 | 0 | 0 | 0 | 0 | 0 |
|  | C | 0 | 0 | 0 | 0 | 4.5 | 3.5 | 4.5 | 1.5 | 2 | 0.5 | 1 | 0 |
| 14 | T | 0.5 | 0 | 1 | 1 | 4 | 3 | 2 | 1 | 1 | 1 | 0.5 | 0 |
|  | R | 0 | 0 | 2 | 2 | 4 | 3 | 2 | 1 | 2 | 0.5 | 1 | 0 |
|  | C | 2 | 0 | 3 | 1 | 4 | 3 | 2 | 1 | 2 | 0.5 | 1 | 0 |
| 15 | T | 2 | 0 | 1 | 1 | 5 | 3 | 1 | 0 | 1 | 0 | 0.5 | 0 |
|  | R | 0 | 0 | 3 | 1 | 5 | 4 | 0 | 0 | 0 | 0 | 0 | 0 |
|  | C | 3 | 0 | 3 | 1 | 5 | 4 | 1 | 0 | 1 | 0 | 1 | 0 |
| 16 | T | 1 | 0 | 0 | 0 | 4 | 3 | 2 | 2 | 1.5 | 0 | 1.5 | 1 |
|  | R | 0 | 0 | 0 | 0 | 5 | 4 | 0 | 0 | 0 | 0 | 0 | 0 |
|  | C | 3 | 0 | 2 | 1 | 5 | 4 | 3 | 2 | 3 | 0 | 3.5 | 1 |
| 17 | T | 1 | 0 | 0 | 0 | 4 | 0 | 2 | 2 | 1 | 0.5 | 0.5 | 0 |
|  | R | 0 | 0 | 0 | 0 | 4.5 | 0 | 0 | 0 | 0 | 0 | 0 | 0 |
|  | C | 1.5 | 1.5 | 1 | 1 | 4 | 2 | 3 | 2 | 1.5 | 0 | 2.5 | 0.5 |
| 18 | T | 3 | 1 | 2 | 1 | 4 | 4 | 1 | 1 | 0 | 0 | 1 | 0 |
|  | R | 0 | 0 | 3 | 3 | 4 | 2 | 2 | 1 | 0 | 1 | 1 | 2 |
|  | C | 2 | 1 | 3 | 2 | 5 | 3 | 1 | 1 | 1 | 1 | 2 | 1 |
|  |   | 3 | 1 | 2 | 0 | 4 | 3 | 2 | 1 | 0 | 0 | 0 | 0 |
| 19 | T | 3 | 1 | 2 | 0 | 4 | 3 | 2 | 1 | 0 | 0 | 0 | 0 |
|  | R | 0 | 0 | 0 | 0 | 5 | 3 | 2 | 1 | 0 | 0 | 0 | 0 |
|  | C | 2 | 1 | 2 | 1 | 5 | 5 | 5 | 5 | 3 | 3 | 5 | 3 |
| 20 | T | 2 | 1 | 3 | 3 | 5 | 5 | 5 | 5 | 3 | 3 | 4 | 4 |
|  | R | 3 | 1 | 3 | 2 | 5 | 5 | 5 | 5 | 4 | 4 | 5 | 3 |
|  | C | 1 | 1 | 3 | 2 | 5 | 5 | 5 | 5 | 5 | 5 | 3 | 5 |
| 21 | T | 5 | 4 | 5 | 5 | 5 | 5 | 5 | 5 | 5 | 5 | 5 | 5 |
|  | R | 5 | 1 | 4 | 4 | 5 | 5 | 5 | 5 | 5 | 5 | 5 | 5 |
|  | C | 2 | 1 | 3 | 2 | 4 | 3 | 2 | 1 | 0 | 0 | 0 | 0 |
| 22 | T | 0 | 0 | 0 | 0 | 0 | 0 | 0 | 0 | 0 | 0 | 0 | 0 |
|  | R | 3 | 2 | 3 | 2 | 4 | 3 | 3 | 2 | 0 | 0 | 0 | 0 |
|  | C | 0 | 0 | 1 | 0 | 4 | 3 | 3 | 2 | 1 | 1 | 1 | 0 |
| 23 | T | 0 | 0 | 0 | 0 | 0 | 0 | 0 | 0 | 0 | 0 | 0 | 0 |
|  | R | 1 | 0 | 1 | 0 | 4 | 3 | 4 | 2 | 1 | 1 | 1 | 1 |
|  | C | 2 | 1 | 2 | 1 | 4 | 4 | 2 | 1 | 1 | 1 | 1 | 0 |
| 24 | T | 0 | 0 | 0 | 0 | 5 | 5 | 0 | 0 | 0 | 0 | 0 | 0 |
|  | R | 3 | 1 | 4 | 3 | 5 | 4 | 3 | 1 | 1 | 2 | 1 | 0 |
|  | C | 1 | 1 | 4 | 3 | 5 | 5 | 1 | 0 | 0 | 0 | 0 | 0 |
| 25 | T | 0 | 0 | 5 | 4 | 5 | 5 | 0 | 0 | 0 | 0 | 0 | 0 |
|  | R | 1 | 1 | 5 | 4 | 5 | 5 | 1 | 0 | 0 | 0 | 0 | 0 |
|  | C | 3 | 1 | 3 | 1 | 3 | 2 | 4 | 0 | 1 | 1 | 1 | 0 |
| 26 | T | 0 | 0 | 0 | 0 | 0 | 0 | 0 | 0 | 0 | 0 | 0 | 0 |
|  | R | 3 | 2 | 3 | 1 | 4 | 2 | 4 | 0 | 2 | 2 | 1 | 0 |
|  | C | 3 | 1 | 1 | 1 | 5 | 5 | 2 | 1 | 4 | 0 | 2 | 0 |
| 27 | T | 1 | 0 | 2 | 2 | 5 | 5 | 0 | 0 | 0 | 0 | 0 | 0 |
|  | R | 4 | 1 | 3 | 1 | 5 | 5 | 2 | 1 | 4 | 0 | 3 | 0 |

*Remarks

Affected portions of plant:
T = top portion; R = root portion; C = chlorotic action
The degree of growth inhibition at T and R was defined in term of the following numerical ratings:
- 5: Complete inhibition (Plants were completely killed or no roots appeared)
- 4: 80 % inhibition
- 3: 60 % inhibition
- 2: 40 % inhibition
- 1: 20 % inhibition
- 0: No inhibition (Plants grew as in untreated areas)

Ratings of chlorotic action (C) was taken on a scale as defined below.
- 5: All the test plants completely chlorotic
- 4: 80 % chlorotic
- 3: 60 % chlorotic
- 2: 40 % chlorotic
- 1: 20 % chlorotic
- 0: None chlorotic

EXAMPLE 3

Herbicidal action and rice plant injuring action of a mixture of 3,3-dimethyl-4-methoxybenzophenone (compound No. 5) and S-(β-benzenesulfonylamidoethyl) O,O-diisopropyldithiophosphate (referred to hereinafter as compound A)

Weed inhibition test in rice cultivation (in paddy field)

1. Treatment of under flooded conditions (pre-emergent treatment for weeds)

a. Test weeds barnyard grass, monochoria, toothcup, false pimpernel, flat sedge, water starwort and needle spikerush.

b. Procedure for treatment with plant growth regulant compositions

A wettable powder containing Compound No. 5 and Compound A as the active ingredients was diluted with water and then used for the treatment c. Test method Each of 1/5,000 are Wagner pots was charged with the surface soil from the paddy field where a lot of the above-described test weeds had appeared in the last year, to provide paddy field conditions.

The flooded water was kept at the level of 3 cm. A given amount of the composition to be tested was applicated under flooded conditions. After the treatment for two days 2 bundles (2 seedlings per bundle) per pot of paddy rice seedlings at 2.5 and 3.5 leaves stages were transplanted 2 cm deep from the top soil surface. After cultivation in a glass greenhouse at 15° – 20°C for 30 days, investigations were made on herbicidal effects and injury against rice.

d. Ratings of herbicidal effects and chemical injury

The number of the surviving test weeds in each of the treated and untreated areas (Classified number of surviving test weeds in Table 4) was counted and the individual numbers so counted were summed to give the total number of surviving test weeds in the treated and untreated areas (Total number of surviving test weeds in Table 4). Ratings were given in terms of ratios of the total number of surviving test weeds in the treated areas to the total number, standardized as 100, of the test weeds which grew in untreated areas.

In Table 4, the number of surviving broadleaf weeds is the summed number of surviving monochoria, toothcup, false pimpernel, flat-sedge and water starwort. The injury against rice was also rated on a scale as defined below.

– : No injury
± : Extremely slight injury
+ : Slight injury
++ : Medium injury
+++ : Severe injury Test results are tabulated in Table 4.

compositions were then added dropwise uniformly to the surface of the irrigation water and admixed well with the surface layer soil of 3 cm in depth. After the treatment for 2 days, 2 bundles (2 seedlings per bundle) per pot of aquatic rice seedlings at 2.5 leaves and 3.5 leaves stages were transplanted. After cultivation in a glass greenhouse at 15° – 25°C for 30 days, investigations were made for herbicidal effects and injury against rice.

d. Ratings of herbicidal effects and injury against rice

The same ratings were used as those used in the treatment under irrigation prior to transplantation of rice.

Test results are tabulated in Table 5.

Table 5

| Dose (g/a) of compound No. 5 | + | Dose (g/a) of compound A | Herbicidal activity Number of surviving weeds | | | Total surviving weeds | | Injury against rice plant | |
|---|---|---|---|---|---|---|---|---|---|
| | | | barnyard grass | broad-leaf weeds | needle spikerush | Number | Ratio | 2.5 leaves stage | 3.5 leaves stage |
| 10 | + | 15 | 2 | 3 | 3 | 8 | 4 | — | — |
| 20 | + | 10 | 0 | 0 | 0 | 0 | 0 | ± | — |
| 30 | + | 5 | 0 | 0 | 0 | 0 | 0 | + | — |
| Untreated | | | 74 | 98 | 38 | 200 | 100 | — | — |

EXAMPLE 4

In each of 1/5,000 are Wagner pots was placed a given amount of alluvial paddy field soil and fertilizers supplied in accordance with usual rice cultivation, to provide paddy field conditions usually found in paddy fields during rice plantation. Thereafter, the perennial of slender spikerush were planted in a manner such that a particular number of buds might be present. The irrigation water was kept at the level of about 0.5 cm until germination of slender spikerush was observed and at the level of 3 cm after the germination. At 15th day from the plantation of the perennial of slender spikerush, the treatment of the pots was carried out using a regulant mixture of 3,3'-dimethyl-4-methoxybenzophenone (Compound No. 5) and Simetryne and a regulant mixture of Compound No. 5 and Prometryne. At 32nd day from the treatment, herbicidal effects of the regulant mixtures were examined. The results are shown in Tables 6 and 7.

Table 4

| Dose (g/a) of compound No.5 | Dose (g/a) of compound A | Herbicidal activity | | | Total number of surviving test weeds | Ratio to total number of test weeds grown in untreated area | Injury against rice plant | |
|---|---|---|---|---|---|---|---|---|
| | | Classified number of surviving test weeds | | | | | | |
| | | barnyard grass | Broad-Leaf weeds | Needle spikerush | | | 2.5 leaves stage | 3.5 leaves stage |
| 10 + | 15 | 5 | 3 | 5 | 13 | 6 | — | — |
| 20 + | 10 | 0 | 0 | 0 | 0 | 0 | — | — |
| 30 + | 5 | 0 | 0 | 0 | 0 | 0 | + | ± |
| Untreated | | 101 | 83 | 20 | 203 | 100 | — | — |

2. Treatment of soil incorporation a. Test weeds

The same weed species as used in the example 3-(1).

b. Test compounds

The same compounds as used in the example 3-(1).

c. Test method

Each of 1/5,000 are Wagner pots was charged with the surface soil from the same paddy field as in (1) to provide paddy field conditions while keeping the irrigation water at the level of 2 cm. Given doses of several plant growth regulant Table 6

Herbicidal effects of a regulant mixture of Compound No. 5 and Simetryne

| Dose (g/a) of Compound No. 5 | + | Dose (g/a) of Simetryne | Herbicidal effect on slender spikerush |
|---|---|---|---|
| 20 | + | 2 | 3.0 |
| 30 | + | 3 | 4.75 |
| 40 | + | 4 | 5.0 |
| 20 | — | | 1.0 |
| 30 | — | | 1.5 |
| 40 | — | | 2.0 |
| — | | 2 | 0 |

Table 6-continued
Herbicidal effects of a regulant mixture of Compound No. 5 and Simetryne

| Dose (g/a) of Compound No. 5 | + | Dose (g/a) of Simetryne | Herbicidal effect on slender spikerush |
|---|---|---|---|
| — | | 3 | 1.0 |
| — | | 4 | 2.5 |

Table 7
Herbicidal effects of a regulant mixture of Compound No. 5 and Prometryne

| Dose (g/a) of Compound No. 5 | + | Dose (g/a) of Prometryne | Herbicidal effect on slender spikerush |
|---|---|---|---|
| 20 | + | 2 | 2.75 |
| 30 | + | 3 | 4.5 |
| 40 | + | 4 | 4.75 |
| — | | 2 | 0 |
| — | | 3 | 2.0 |
| — | | 4 | 4.0 |

Remarks:
1) Ratings of herbicidal effect are defined in terms of the following numerals:
5: Completely (100%) killed
4: 80% killed
3: 60% killed
2: 40% killed
1: 20% killed
0: No herbicidal effect (The same number of weeds as in untreated areas survived.)

The following examples illustrate the methods of manufacturing agricultural preparations suitable for practical use.

EXAMPLE 5 Emulsified preparation

A homogeneous emulsion is obtained by mixing 20 parts of an active compound of the invention, 70 parts of a mixture containing equi-amounts of xylene, benzene and dimethylformamide, and 10 parts of a mixture of an alkylphenol polyether alcohol and a calcium alkylbenzenefulfonate.

EXAMPLE 6 Dust preparation

20 Parts of an active compound of the invention, 20 parts of a mixture of diatomaceous earth and finely divided powder of hydrated silicic acid and 60 parts of talc are mixed together and milled to disperse the active compound uniformly into the carrier materials and the resulting mixture is finely divided to give a dust preparation.

EXAMPLE 7 Wettable powder preparation 50 parts of an active compound of the invention are mixed with 30 parts of finely divided powder of hydrated silicic acid and 12 parts of clay, and then mixed homogeneously with 8 parts of a mixture of sodium laurate and sodium dinaphthylmethanesulfonate. The mixture obtained is then milled into finely divided powder.

EXAMPLE 8 Granular preparation

2 Parts of an active compound of the invention are mixed with 35 parts of diatomaceous earth, 23 parts of bentonite, 38 parts of talc and parts of a suitable disintegrator, and the resulting mixture is uniformly wetted by adding 18 parts of water thereto and subjected to granulation by the aid of an extrusion molding machine. After applying the granules obtained to a dry crusher, the size of the granules is rendered uniform to give a granular preparation.

What is claimed is:
1. A compound of the general formula:

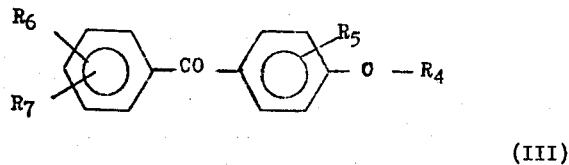

(III)

wherein $R_4$ is a lower alkyl group or allyl group. $R_5$ and $R_6$ each stand for lower alkyl groups and $R_7$ is a hydrogen atom or a lower alkyl group.

2. A compound according to claim 1 wherein $R_4$ is a lower alkyl group or allyl group, $R_5$ is a lower alkyl group, $R_6$ is methyl group and $R_7$ is hydrogen atom.

* * * * *